United States Patent [19]

Walker et al.

[11] Patent Number: 4,670,473
[45] Date of Patent: Jun. 2, 1987

[54] SYN GAS CONVERSION

[75] Inventors: Robert H. Walker, Chicago; David A. Palmer, Naperville; Donna M. Salvatore, Chicago; Edward J. Bernier, Naperville, all of Ill.

[73] Assignee: Amoco Corporation, Chicago, Ill.

[21] Appl. No.: 764,425

[22] Filed: Aug. 9, 1985

[51] Int. Cl.⁴ ............................................. C07C 27/06
[52] U.S. Cl. ................................. 518/706; 518/712; 518/714; 518/713; 518/715; 568/502
[58] Field of Search ................... 568/902 H; 518/706, 518/712, 714, 713, 715

[56] References Cited

U.S. PATENT DOCUMENTS

| | | | |
|---|---|---|---|
| 1,859,244 | 5/1932 | Patar | 518/713 |
| 4,096,164 | 6/1978 | Ellgen | 568/902 H |
| 4,346,179 | 8/1982 | Sugier et al. | 518/712 |
| 4,367,206 | 1/1983 | Pinto | 518/706 |
| 4,386,009 | 5/1983 | Feder et al. | 568/902 H |

FOREIGN PATENT DOCUMENTS

| | | | |
|---|---|---|---|
| 119609 | 9/1984 | European Pat. Off. | |
| 2506299 | 11/1982 | France | 518/713 |
| 2036739 | 7/1980 | United Kingdom | 568/902 H |

OTHER PUBLICATIONS

Hougen et al, "Chemical Process Principles", Part 3, Kinetics & Catalysis, John Wiley & Sons, 1947, pp. 1031–1033.

*Primary Examiner*—Howard T. Mars
*Attorney, Agent, or Firm*—William H. Magidson; Ralph C. Medhurst

[57] ABSTRACT

Conversion of syn gas to methanol and higher alkanols wherein alkanols are added to a syn gas reactor. Lower alkanols are homologated to higher alkanols. Liquid methanol is added as an interstage quench.

12 Claims, No Drawings

SYN GAS CONVERSION

This invention relates to the conversion of syn gas to methanol and higher alkanols wherein alkanols are added to a syn gas reactor. More particularly, this invention relates to the conversion of syn gas to alkanols wherein methanol is separated from at least some higher alkanols and recycled to a syn gas reactor or reactors.

Numerous processes have been proposed for making mixed alkanols from syn gas or $H_2/CO$. These processes typically produce a significant concentration of methanol, not uncommonly in excess of 50 wt. %. The principal proposed use for these alkanol mixtures is as fuel components in gasolines since they function as octane boosters and can replace lead. However, methanol has significant drawbacks. For example, the BTU value of methanol is approximately 60% of gasoline on a volume basis, whereas the higher alkanols (ethanol, etc.) have in excess of 70% of the BTU value of gasoline. Further, numerous automobile manufacturers have taken the position that new car engine warranties are void if fuels containing methanol are used, whereas ethanol and other higher alkanols can be used in prescribed concentrations without voiding warranties. Some gasolines in the United States contain as much as 10% by volume ethanol. Methanol is also considered undesirable in increasing evaporative emissions. Accordingly, there is a need for techniques to reduce the amount of co-produced methanol in syn gas conversions.

At the present time, there are two major types of reactors used commercially to convert syn gas to alkanols. One of these, which is called a Lurgi-type reactor, contains in excess of 1,000 tubes of catalyst surrounded by a heat sink through which the syn gas passes. These reactors are relatively expensive but it is possible to obtain about a 40% conversion of syn gas per pass through the reactor. A more common, so-called ICI reactor employs a series of three or more catalyst beds. As pointed out by SRI, a typical ICI reactor is operated by compressing approximately one-third of the syn gas to about 240 to 1,500 psi and adding the compressed gas at about 470° F. to the first catalyst bed. The other two-thirds of the syn gas is added to the reactor system at three or more levels in the catalyst bed as an interstage quench to cool down the exothermic reaction. Heat removal generally limits conversion by the ICI reactor to about 20% per pass. Accordingly there is a need for increasing the percent conversion per pass in syn gas reactors having more than one catalyst bed.

The general object of this invention is to provide an improved process of producing alkanols from syn gas containing relatively lower levels of co-produced methanol. A more specific object of this invention is to provide a method for increasing the conversion per pass of syn gas in reactors containing more than one catalyst bed. Other objects appear hereinafter.

We have now found that the objects of this invention can be attained by adding alkanols to a syn gas reactor. Preferably the alkanols, containing at least some methanol, are separated from the alkanol product stream and recycled to the syn gas reactor. Advantageously, this technique can be employed with any reactor capable of converting syn gas to alkanols including the so-called Lurgi or ICI reactors. If lower alkanols, such as methanol and ethanol, are recycled to the reactor, some of the lower alkanols homologate to higher alkanols. In some cases, it can be advantageous to continuously recycle methanol to extinction in the syn gas reactors. In other cases, methanol can be separated from the alkanols and sold separately.

In a particularly advantageous aspect of this invention, alkanols, particularly methanol, are employed as an interstage quench instead of, or together with, syn gas. Since the alkanols, and particularly methanol, are a more effective quench than syn gas in interstage cooling, it is possible to increase the rate of conversion per pass in reactors containing more than one catalyst bed to 25% or more, which is extremely significant. For example, by quenching with methanol, especially liquid methanol, a much greater reduction in temperature can be obtained for a given amount of quench material. The heat of vaporization of methanol is approximately 250 cal/gm or about 1000 times the specific heat of the mixture of carbon monoxide (0.25 cal/gm per degree centigrade) and hydrogen (3.4 cal/gm per degree centigrade) normally used for interstage quenching.

In somewhat greater detail, this invention comprises converting syn gas to alkanols in a reactor, separating at least part of the methanol from the product stream and adding at least part of the separated methanol back to the syn gas reactor.

Virtually any catalyst capable of converting syn gas to alkanols can be used in this invention. For example, the molybdenum type catalysts disclosed in U.S. Pat. Nos. of Murchison et al 4,151,190, Murchison et al 4,199,522, Stewart 2,490,488, and 2,539,414; the chromium/manganese oxide catalyst promoted with alkali disclosed in G. T. Morgan et al, J. Soc. Chem. Eng., Volume 51, 1932, Jan. 8, pp 1 TIT; rhodium catalysts, such as those described in U.S. Pat. No. 4,014,913, containing rhodium and thorium or uranium or iron or molybdenum or tungsten, U.S. Pat. No. 4,096,164, which discloses the use of rhodium in combination with molybdenum or tungsten, European Patent Application No. 81-33,212, which discloses using rhodium in combination with one or more metals, European Patent Application No. 79-5,492, which discloses the production of alkanols using copper, thorium, alkali metal promoter and an additional metal, all of which are hereby incorporated by reference. The preferred catalysts for use in this invention are those disclosed in European Patent No. 119,609, and Pietro et al U.S. Pat. No. 4,481,012 which are hereby incorporated by reference. European Patent No. 119,609 discloses a catalyst comprising (1) at least one element selected from the group consisting of molybdenum, tungsten, rhenium in free or combined form;
(2) a promoter comprising an alkali metal, an alkaline earth element in free or combined form; and optionally
(3) a support; which is capable of forming an alkanol fraction boiling in the range of motor gasoline. These catalysts can produce high yields of $C_1$ to $C_4$ alkanols and as much as 0.3 weight parts of alkanol per hour per weight part of catalyst can be achieved. Due to high selectivity and water shift conversion activity of the catalyst, separation of the methanol from the other alkanols is facilitated.

The second class of preferred catalysts comprise base promoted zinc/chromium and base promoted copper/zinc which produce more propanol and butanol than ethanol thereby facilitating separation of methanol from ethanol.

The first component of the first preferred class of catalysts comprises at least one member selected from the group consisting of molybdenum, tungsten, rhenium, and mixtures thereof in free or combined form. The molybdenum, tungsten or rhenium can be present in the catalyst in "free or combined form" as a metal, an alloy or a compound of the element. Representative compounds include the sulfides, carbides, oxides, halides, nitrides, borides, salicylides, oxyhalides, carboxylates such as acetates, acetyl acetonates, oxalates, etc., carbonyls, and the like. Representative compounds also include the elements in anionic form such as molybdates, phosphomolybdates, tungstates, phosphotungstates, and the like, and include the alkali, alkaline earth, rare earth and actinide series salts of these anions. The sulfides, carbonyls, carbides and oxides are preferred with the sulfide being most preferred. While many catalysts useful in this invention require feed gas containing less than 100 ppm sulfur, molybdenum catalysts are relatively sulfur tolerant and are not adversely affected by up to 10 ppm sulfur in the $H_2/CO$ feed.

The molybdenum, tungsten or rhenium can be present in an amount based on the weight of the total catalyst of at least two percent, preferably at least 5 percent with an upper limit of 70 percent and preferably 30 percent of the total catalyst when the catalyst is supported. When unsupported molybdenum, tungsten or rhenium is present, it can be present in about stoichiometric quantities in relation to other elements with which it is combined as a compound.

The promoter can comprise one or more alkali metal or alkaline earth metal elements in free or combined form. Alkali metal elements include lithium, sodium, potassium, rubidium and cesium. Alkaline earth metal elements include beryllium, magnesium, calcium, strontium and barium. Alkali metal elements and in particular sodium and potassium are preferred. Potassium is most preferred.

The promoter can be present in free or combined form as a metal, oxide, hydroxide, sulfide or as a salt or a combination of these. The promoter is preferably present at a level sufficient to render the support or the bulk catalyst neutral or basic. The promoter is generally present, based on the weight of the finished catalyst, in an amount of at least 0.05 weight percent as a free element in the finished catalyst. Preferably it is present in an amount of at least 0.1 percent and most preferably at least 0.5 percent. Large amounts up to 20 percent of the promoter can be present. Preferably the promoter is present at less than 10 percent.

The promoter can be added as an ingredient to the molybdenum, tungsten, or rhenium component or to the support, or can be part of one of the other components such as sodium or potassium molybdate or as an integral part of the support. For example, carbon supports prepared from coconut shells often contain small amounts of alkali metal oxides or hydroxides or the support may contain a substantial amount of the promoter such as when the support is magnesia. If desired the promoter can be added to the syn gas feed.

An optional third component of the first preferred class of catalyst is a support which can assume any physical form such as pellets, granules, beads, extrudates, etc. The supports can be coprecipitated with the active metal species, or the support in powder form can be treated with the active metal species and then used as is, or formed into the aforementioned shapes, or the support can be formed into the aforementioned shapes and then treated with the active catalytic species.

The catalyst can be dispersed on the support by methods known in the art. Examples include impregnation from solution, vapor deposition, intimate physical mixing and the like. One or more of these methods can be used. A preferred method of depositing the catalytic species on a support is a combination of an incipient wetness technique and physical mixing with decomposition of a carbonyl.

A first step in the preferred method of placing the catalyst and/or promoters on the support is called the incipient wetness technique. Water- or solvent-soluble salts of the metals to be dispersed on the support are dissolved in a quantity of solvent which can be aqueous, nonaqueous, or a mixed solvent. A sufficient quantity of the resulting solution is added to the support in an amount no more than will be completely absorbed by the support. The solvent is then evaporated to leave the salt dispersed on the support. Depending on the solubility of the salt chosen and on the quantity of the element desired to be dispersed on the support, this process can be performed once or several times. Impregnations with two or more promoters can be performed by codissolving them in the solvent or by adding them separately in different quantities or types of solvent. In addition to evaporating the solvent, the loaded support can be heated in air, hydrogen, nitrogen or other atmosphere to obtain the catalytic species in their final form. Reduction in hydrogen at mildly elevated pressures at from 250° C. to 500° C. is preferred. The wetting, evaporating and heating steps can be repeated several times in order to achieve the desired concentration of catalytic species or promoter on the support.

In the second step of the preferred method, a carbonyl of the metal to be dispersed is dry mixed with the resultant metal on a support from the incipient wetness impregnation step. This metal can be the same or different from the first metal. After intimate mixing, the mixture is calcined in flowing nitrogen to drive off CO and yield the catalyst ready for use.

Suitable supports include basic oxides, silica, carbon, or suitable solid compounds of magnesium, calcium, strontium, barium, scandium, yttrium, lanthanum and the rare earths, titanium, zirconium, hafnium, vanadium, niobium, tantalum, thorium, uranium, and zinc. Preferably the supports are neutral or basic or can be rendered neutral or basic by addition of the alkaline promoters. The silicas include, for example, silica gel, diatomaceous earth, and crystalline silicates.

The carbon supports, which are preferred, include activated carbons such as those prepared from coals and coal-like materials, petroleum-derived carbons and animal- and vegetable-derived carbons. Preferably, the carbon support has a surface area of 1-1500 $m^2/g$ as measured by the BET nitrogen test. Preferably, micropores (<20 Å (<2 nm)) are minimized and at least twenty percent of the volume of the pores is comprised of pores having a diameter of from about 20 Å (60 nm). Examples include coconut shell charcoal, coals, petroleum cokes, carbons formed by pyrolyzing materials such as vinylidene chloride polymer beads, coal, petroleum coke, lignite, bones, wood, lignin, nut shells, petroleum residues, charcoals, etc.

Based upon the weight of the total catalyst, the support when present generally comprises at least 20 percent of the catalyst and usually not more than 98 percent of the catalyst. Preferably, the support comprises at least 50 wt. % and most preferably at least 70 wt. % of the catalyst.

Molybdenum sulfide catalysts can be made by thermal decomposition of ammonium tetrathiomolybdate or other thiomolybdates as disclosed in U.S. Pat. No. 4,243,553; from purchased active molybdenum sulfides or by calcining $MoS_3$. Preferred is the decomposition of ammonium tetrathiomolybdate formed by precipitation from a solution of ammonium heptamolybdate with ammonium sulfide, followed by spray drying and calcining to form the molybdenum sulfide. The molybdenum sulfide can also be precipitated directly on to a support. Tungsten or rhenium sulfides can be similarly made. An unsupported catalyst preferably has a surface area of at least 10 $m^2/g$, and more preferably more than 20 $m^2/g$ as measured by the BET nitrogen surface area test.

The promoter can be added to the active catalytic element prior to, during, or after the formation of the sulfide by physical mixing or solution impregnation. The active metal sulfide can then be combined with binders such as bentonite clay, and/or pelleting lubricants such as Sterotex® and formed into shapes for use as a catalyst.

The finished catalyst can be used in a fixed bed, moving bed, fluid bed, ebullated bed, or a graded bed wherein concentration and/or activity of the catalyst varies from inlet to outlet in similar manner to known catalysts. The catalyst can be used in powdered form or may be formed into shapes with or without a binder.

The preferred catalysts of the invention can be employed individually or in combination with other catalysts and activators for the claimed process. In general, the preferred catalysts when used alone have numerous advantages. On the other hand, in combination with conventional catalysts, they tend, progressively, to modify the usual effects in accordance with their individual characteristics, so that quantitatively intermediate results can be achieved. In short, the preferred catalysts can be combined, for example, with typical hydrogenation catalysts such as cobalt and nickel, and with dehydration catalysts such as aluminas and zeolites to effect desired additional results.

However, the preferred catalysts preferably contain less than 25 wt. %, based on the total weight of carbon oxide hydrogenation active metals, of other carbon oxide hydrogenation active metals. Suitable hydrogenating components present in limited quantities are preferably those that contain chromium, manganese, iron, cobalt, copper, zinc, ruthenium and rhodium.

Under preferred conditions the catalyst is stable for long periods of time and under ideal conditions can be stable and active for as many as 3000 hours or more. Activity and selectivity are preferably substantially retained after 100 hours of operation, more preferably after 500 hours, and most preferably after 1000 hours operation. In the case of reduced oxide catalysts, declines in activity and selectivity can generally be regenerated by reduction with hydrogen, after which the catalyst can regain most of its original activity and be used for another long period of time before regenerating again.

Under preferred conditions, the weight units per hour of alkanols boiling in the range of motor gasoline per weight unit of catalyst can exceed 0.2. Under ideal conditions, it can exceed 0.25 and even 0.3.

Of the alkanols formed with supported molybdenum catalysts without recycle, the largest single component is methanol which is typically above 20 wt. % of the alkanol fraction and generally above 40 wt. %, but generally less than 70 wt. % and preferably less than 60 wt. % of the alkanols formed. The next most abundant component can be ethanol which is typically greater than 15 wt. % of the alkanol fraction and often approaches or exceeds 30 wt. %. The $C_5+$ alkanols are generally 10 wt. % or less of the alkanol fraction.

The hydrogen and carbon monoxide suitable for use in this invention can be obtained from any source, such as gasification of hydrocarbonaceous materials (coal, high specific gravity oils, or natural gas); as a by-product of partial combustion cracking of hydrocarbons; by steam reforming of liquid or gaseous hydrocarbons; through the water-gas shift reaction; or some combination of these. The hydrogen and carbon monoxide can also be generated separately and combined. The molar ratio of hydrogen to carbon monoxide in the feed gas which contacts the catalyst ranges generally from 0.25:1 to 100:1, preferably from 0.5:3 to 3:1.

The mole ratio of alkanol comprising at least 80 mole percent methanol to carbon monoxide added to a continuous reactor or first catalyst bed of a multi-catalyst bed reactor can range from 0.2:1 to 0.7:1. The mole ratio of alkanol comprising at least 80 mole percent methanol to total moles of $H_2$ and CO added as an interstage coolant can range from infinity (substantially no CO or $H_2$) to as little as 1%, preferably in the liquid state. Generally, the mole ratio of interstage alkanol coolant to interstage total moles carbon monoxide and hydrogen coolant ranges from 1:9 to 7:3 depending upon the desired degree of interstage cooling and desired ultimate product composition. In either case, the alkanol (methanol rich stream) can be mixed with CO and/or hydrogen or added separately to the reactor. By using, the methanol rich stream as an interstage coolant, processes using catalyst beds can be modified to have substantially all the syn gas added to the first catalyst bed.

As indicated above, this invention comprises broadly reacting syn gas in contact with a catalyst capable of converting syn gas to alkanols in a reactor under suitable conditions to form alkanols, partitioning at least part of the lower alkanols, preferably methanol, from the alkanol product stream and recycling alkanol preferably comprising at least 80 mole percent methanol to the reactor. The methanol can be mixed with syn gas and added to the reactor or can be added separately to the reactor without mixing with the syn gas.

Generally, the selectivity to alkanols with the catalyst is dependent on the pressure. In the normal operating ranges, the higher the pressure at a given temperature, the more selective the process is to alkanols. The minimum gauge pressure is about 500 psig (3.55 MPa). The preferred minimum is 750 psig (5.27 MPa) with 1,000 psig (7.00 MPa) being a more preferred minimum. While 1,500 psig (10.45 MPa) to 4,000 psig (27.7 MPa) is the most desirable range, higher pressures can be used and are limited primarily by cost of the high pressure vessels and compressors needed to carry out the higher pressure reactions. A typical maximum is 10,000 psig (69.1 MPa) with 5,000 psig (34.6 MPa) a more preferred maximum. A most preferred operating pressure is 3,000 psig (20.8 MPa) for unsupported $MoS_2$ catalysts.

The selectivity to alkanols with the catalyst is also a function of temperature and is interrelated with the pressure function. The minimum temperature used is governed by productivity considerations and the fact that at temperatures below about 200° C. volatile catalytic metal carbonyls can form. Accordingly, the minimum temperature is generally 200° C.

At a constant pressure, as the temperature increases, the selectivity to alkanols decreases. In other words, at lower pressures one is limited to lower maximum temperatures in order to obtain a given selectivity. For example, at 500 psig (5.27 MPa), the maximum temperature to obtain a net selectivity to alkanols of greater than 20 percent is 325° C. At 1,000 psig (7.00 MPa), a net selectivity of 20 percent or more may be achieved at a temperature of 350° C. or less. At a pressure of 1,500 psig (10.45 MPa), a net selectivity to alkanols of 20 percent or greater can be obtained at 375° C. or less. At higher pressures, one can obtain 20 percent selectivity at up to 400° C. However, the preferred range of operation is from 240° C. to 325° C.

The $H_2$/CO gas hourly space velocity (GHSV) is a measure of the volume of hydrogen plus carbon monoxide gas at standard temperature and pressure passing a given volume of catalyst in an hour's time. This can range from 100 to 10,000 hour$^{-1}$ and preferably from 300 to 5,000 hour$^{-1}$. Selectivity to the alkanols generally increases as the space velocity increases. However, conversion of carbon monoxide decreases as space velocity increases.

Preferably at least a portion of the unconverted hydrogen and carbon monoxide in the effluent gas from the reaction, more preferably after removal of product alkanols, water and carbon dioxide formed, is recycled to the reactor.

The alkanol product stream can be recycled to the syn gas reactor to homologate the lower alkanols to higher alkanols, preferably after separation of water and carbon dioxide and still more preferably after separation of the lower alkanols to form a recycle product stream containing at least 80 mole percent methanol. As indicated above, methanol can advantageously be recycled to extinction to produce a product substantially free of methanol suitable for use as a desirable gasoline blending stock. The lower alkanol product stream is more advantageously liquified and recycled as an interstage coolant for use in syn gas reactor systems containing catalyst beds.

In addition, the synthesis can be carried out at as little feed conversion per pass as is compatible with economic constraints related to the separation of the alkanol product from unreacted feed and hydrocarbon gases. Accordingly one can increase the space velocity and recycle ratios to preferably obtain about 25-50% conversion per pass.

With preferred catalysts and under preferred conditions of temperatures, pressures, $H_2$/CO ratio, GHSV and recycle ratio, 0.1 or more weight parts of alkanols per hour can be formed per weight part of catalyst. Under the more preferred conditions of 300° C., 1,500 psig (10.3 MPa), 5,000$^{-1}$ and a $H_2$/CO ratio of 1.25:1, with a Mo/K on carbon catalyst, 0.3 weight parts of alkanol or more per hour per weight part of catalyst can be obtained. Under the most preferred conditions of 280° C., 3,000 psig (20.7 MPa), a GHSV of 5,000 and a $H_2$/CO ratio of 1.2; with a bulk $MoS_2$ catalyst, 0.6 wt parts of alkanols or more per hour per weight part of catalyst can be obtained.

Under the most preferred conditions, alkanols can be obtained in about an 85 percent $CO_2$ free carbon selectivity. The $CO_2$ free carbon selectivity is defined as 100 times the moles of carbon present in a product fraction divided by the total moles of carbon in all products which are not $CO_2$ or unconverted feed. For example, if one mole of ethanol is found in the alkanol fraction, this is counted as 2 moles of carbon. Carbon dioxide and water are not counted as products in this calculation.

EXAMPLE I

This example illustrates the homologation of methanol by introducing methanol and syn gas into a reactor employing a potassium carbonate promoted molybdenum sulfide catalyst. The reactor used in this example contains two flow control loops, one for the hydrogen feed, and one for the carbon monoxide; a 4-zone furnace for temperature control; a traveling thermocouple mounted on the single axis of the catalyst bed for monitoring temperature; a pressure control loop; dry ice product traps for condensing alkanols; a wet test meter to monitor effluent gas flow rates; and a microprocessor to control variables and collect all the data of the unit. The promoted molybdenum disulfide catalyst was prepared by pelletizing 66% by weight molybdenum disulfide, 10% by weight potassium carbonate, 20% by weight bentonite clay and 4% by weight Sterotexr® pelleting lubricant into about 3.2 millimeter diameter pellets. The catalyst was initially brought on stream in the fixed bed reactor at 3,000 hourly space velocity, 1,500 psig at 550° F. with a feed $H_2$/CO ratio of 1:16 and 40 ppm $H_2S$ partial pressure. Under these conditions the carbon monoxide conversion was approximately 45%. After the temperature was lowered to 490° F. the CO conversion dropped to approximately 20% to simulate a commercial size fixed bed reactor. After the reactor was lined out for 76 hours the pressure was 1,501 psig, temperature 491° F., 2,990 hourly space velocity, 1.15 $H_2$/CO molar ratio and 27% conversion of H and CO. The carbon monoxide was converted to 15.5% $C_2$ to $C_4$ hydrocarbons, 56.9% alkanols, and 27.5% methane on a $CO_2$ free basis. Methanol recycle was then simulated by adding 1.07 grams per hour methanol to the feed gas. The product stream contained 16.1% by weight CO converted to $C_2$ to $C_4$ hydrocarbons, 55.9% by weight alkanols, and 28% by weight methane on a carbon dioxide free basis. Methanol addition was then stopped and the feed gas $H_2$/CO ratio was set to 2.37. The $H_2$ plus CO conversion was 37.1%. The carbon monoxide was converted to 17.2% $C_2$ to $C_4$ hydrocarbons, 59.0% alkanols, and 23.8% methane on a carbon dioxide free basis. The simulated alkanol recycle carbon balance is set forth below in Table I.

TABLE I

|  | Before Methanol Addition | During Methanol Addition |
|---|---|---|
| IN |  |  |
| CO | 8.69 | 8.69 |
| $CH_3OH$ | — | 0.40 |
| Total | 8.69 | 9.09 |
| OUT |  |  |
| CO | 5.66 | 5.69 |
| $CO_2$ | 1.07 | 1.13 |
| $CH_4$ | 0.42 | 0.52 |
| $C_2$-$C_4$ | 0.34 | 0.30 |
| $CH_3OH$ | 0.11 | 0.19 |
| $C_2H_5OH$ | 0.19 | 0.26 |
| $C_3H_7O_4$ | 0.10 | 0.11 |
| $C_4H_9OH$ | 0.06 | 0.06 |
| $C_5H_{11}OH$ | 0.01 | 0.01 |
| $C_6H_{13}OH$ | 0.01 | — |
| Total | 7.97 | 8.27 |
| % Recovery | 91.7 | 91.0 |

The above table clearly shows that the production of ethanol an dpropanol was increased by the simulated recycle of methanol to the syn gas reactor.

EXAMPLE II

The process described in Example I was carried out in essentially the same manner except that the catalyst pellets comprised 66 wt. % of a mixture of cobalt sulfide and molybdenum disulfide, 10 wt. % of potassium carbonate, 20 wt. % bentonite clay, and 4 wt. % Sterotex ®. This catalyst was brought on stream at 3,000 hourly space velocity, 15,000 psig, 530° F. with a feed $H_2/CO$ ratio of 1:16 and 40 ppm partial pressure of hydrogen sulfide. At these conditions the carbon monoxide conversion was only 15%, so that the temperture was raised to 564° F. raising the conversion to about 20%. The hourly spaced velocity was then reduced to 1,500 and the feed $H_2/CO$ ratio was reduced to 1.08 yielding a CO conversion of 22%. After obtaining steady state data methanol recycle was simulated by adding methanol to the feed stream at a rate of 0.79 g/hr. The product distributions are set forth below in Table II.

TABLE II

|  | Before Methanol Addition | During Methanol Addition | After Methanol Addition |
|---|---|---|---|
| IN | | | |
| CO | 8.69 | 8.69 | 8.69 |
| $CH_3OH$ | — | 0.30 | — |
| Total | 8.69 | 8.99 | 8.69 |
| OUT | | | |
| CO | 7.20 | 7.26 | 7.58 |
| $CO_2$ | 0.32 | 0.52 | 0.33 |
| $CH_4$ | 0.10 | 0.16 | 0.10 |
| $C_2$-$C_5$ | 0.12 | 0.19 | 0.11 |
| $CH_3OH$ | 0.14 | 0.23 | 0.17 |
| $C_2H_5OH$ | 0.15 | 0.24 | 0.17 |
| $C_3H_7OH$ | 0.05 | 0.08 | 0.06 |
| $C_4H_9OH$ | 0.01 | 0.01 | 0.01 |
| $C_5H_{11}OH$ | — | — | — |
| Total | 8.09 | 8.69 | 8.53 |
| % Recovery | 93.1 | 96.7 | 98.2 |

The above data clearly shows that methanol is converted to higher alkanols during the time the methanol recycle is simulated.

EXAMPLE III

This example simulates interstage cooling using 100% liquid methanol recycle and a feed sufficient to produce 100 lbs/hour of $C_2$ or higher alcohols using an ICI type reactor at 564° F. and three catalyst beds of the molybdenum disulfide catalyst used in Example I wherein the feed for the first catalyst bed comprises two-thirds of composition M comprising (a) fresh make up feed of 886 lbs/hour carbon monoxide (92.9 wt % CO) and 68 lbs/hour hydrogen (7.1 wt % $H_2$) and (b) recycle composition comprising 2709 lbs/hour carbon monoxide (79.0 wt % CO), 224 lbs/hour hydrogen (6.5 wt % $H_2$), 207.5 lbs/hour carbon dioxide (6.1 wt % $CO_2$), 135.9 lbs/hour methane (4.0 wt %), 98.8 lbs/hour ethane (2.9 wt %), 37.1 lbs/hour propane (1.1 wt %) and 12.4 lbs/hour butane (0.4 wt %); the last two catalyst beds are each cooled with one-six of composition M and 48.5 lbs/hour recycled liquid methanol (0.03 moles of methanol per mole of carbon monoxide added to the reactor) at 16% conversion. The liquid methanol for recycle is obtained by separating 97 lbs/hour methanol from 100 lbs/hour higher alcohols (75.8% ethanol, 21.2% propanol and 3.0% butanol) and 2.7 lbs/hour water. If liquid methanol is not used as a quench only one-third of composition M can be added to the reactor as feed while the remaining two-thirds of composition M is added as interstage quench.

We claim:

1. The process of conversion of syn gas to alkanols which comprises reacting carbon monoxide and hydrogen to form alanols in the presence of at least two beds of catalyst capable of converting syn gas to alkanols in a syn gas reactor(s), adding lower akanols comprising methanol as an interstage coolant between at least two catalyst beds.

2. The process of claim 1, wherein the lower alkanols are in a liquid state.

3. The process of claim 2, wherein the mole ratio of lower alkanol to total moles of hydrogen and carbon monoxide added as an interstage coolant ranges from infinity to 0.01.

4. The process of claim 2, wherein the mole ratio of lower alkanol to total moles of hydrogen and carbon monoxide added as an interstage coolant ranges from 1:9 to 7:3.

5. The process of claim 4, wherein the catalyst comprises at least one element selected from the group consisting of molybdenum, tungsten, and rhenium in free or combined form and a promoter comprising at least one member selected from the group consisting of an alkali metal and an alkaline earth metal in free or combined form.

6. The process of conversion of syn gas to alkanols which comprises reacting carbon monoxide and hydrogen to form alkanols in the presence of a catalyst capable of converting syn gas to alkanols in a syn gas reactor(s), separating lower alkanols comprising methanol from the product stream and recycling said lower alkanols as an interstage coolant between at least two catalyst beds in the syn gas reactor(s).

7. The process of claim 6, wherein the lower alkanols are in a liquid state.

8. The process of claim 7, wherein the mole ratio of lower alkanol to total moles of hydrogen and carbon monoxide added as an interstage coolant ranges from infinity to 0.01.

9. The process of claim 7, wherein the mole ratio of lower alkanol to total moles of hydrogen and carbon monoxide added as an interstage coolant ranges from 1:9 to 7:3.

10. The process of claim 9, wherein the catalyst comprises at least one element selected from the group consisting of molybednum, tungsten, and rhenium in free or combined form and a promoter comprising at least one member selected from the group consisting of an alkali metal and an alkaline earth metal in free or combined form.

11. The proces of claim 1 wherein the conversion of syn gas to alkanols is carried out in the presence of at least three beds of catalysts and methanol is added as interstage coolants between at least three catalyst beds.

12. The process of claim 6 wherein the conversion of syn gas to alkanols is carried out in the presence of at least three beds of catalysts and methanol is added as interstage coolants between at least three catalyst beds.

* * * * *

UNITED STATES PATENT OFFICE
CERTIFICATE OF CORRECTION

Patent No. 4,670,473      Dated June 2, 1987

Inventor(s) ROBERT H. WALKER, DAVID A. PALMER, DONNA M. SALVATORE AND EDWARD J. BERNIER It is certified that error appears in the above-identified patent and that said Letters Patent are hereby corrected as shown below:

| PATENT Column | Line | |
|---|---|---|
| 2 | 47 | "reference. European" should read ---reference. (new paragraph) European--- |
| 2 | 56 | "(3) a support; which" should read ---(3) a support; (new paragraph) which--- |
| 6 | 35 | "By using, the" should read ---By using the--- |
| 8 | 35 | "H and" should read ---$H_2$ and--- |
| 9 | 2 | "an dpropanol" should read ---and propanol--- |
| 9 | 13 | "and 40" should read ---and a 40--- |
| 9 | 17 | "hourly spaced velocity" should read ---hourly space velocity--- |
| Claim 1 | 3 | "alanols" should read ---alkanols--- |
| Claim 11 | 1 | "proces" should read ---process--- |

Signed and Sealed this

First Day of September, 1987

Attest:

DONALD J. QUIGG

Attesting Officer      Commissioner of Patents and Trademarks